United States Patent [19]

Lucas et al.

[11] Patent Number: 4,690,719
[45] Date of Patent: Sep. 1, 1987

[54] EGG TIMER-SHAPED ABSORBENT PAD FOR A PAIR OF NAPPY-PANTS, AND PROCESS FOR THE CONTINUOUS MANUFACTURE OF SUCH PADS

[75] Inventors: Gérard Lucas, Bousbecque; Jacques Dussaud, La Madeleine; André Leroy, Bousbecque, all of France

[73] Assignee: Boussac Saint Freres B. S. F., Lille, France

[21] Appl. No.: 900,642

[22] Filed: Aug. 26, 1986

[30] Foreign Application Priority Data

Aug. 27, 1985 [FR] France ............................... 85 12808

[51] Int. Cl.$^4$ .............................................. B32B 1/00
[52] U.S. Cl. .................................... 156/201; 156/204; 156/250; 156/257; 604/378; 604/385 R
[58] Field of Search ................................. 604/378–380, 604/385.1, 385.2, 368; 156/200–202, 204, 257, 271, 211, 62.6, 280; 493/396–401, 413, 162

[56] References Cited

U.S. PATENT DOCUMENTS

| | | |
|---|---|---|
| 2,122,417 | 7/1938 | Fridolph . |
| 3,559,648 | 2/1971 | Mason .............................. 604/378 X |
| 4,381,782 | 5/1983 | Mazurak et al. ............. 604/385.2 X |
| 4,410,324 | 10/1983 | Sabee ............................ 604/385.2 X |
| 4,425,127 | 1/1984 | Suzuki et al. ................ 604/385.2 X |
| 4,500,316 | 2/1985 | Damico ........................ 604/385.1 X |

*Primary Examiner*—David Simmons
*Attorney, Agent, or Firm*—Armstrong, Nikaido, Marmelstein & Kubovcik

[57] ABSTRACT

Absorbent pad of triple thickness in the between-the-legs zone (7) and of single thickness in the lateral parts of the end zones (5,6), formed from a rectangular piece of absorbent material comprising incisions in the end zones and subjected to a double folding around longitudinal lines connecting between them the incisions of the two end zones.

8 Claims, 8 Drawing Figures

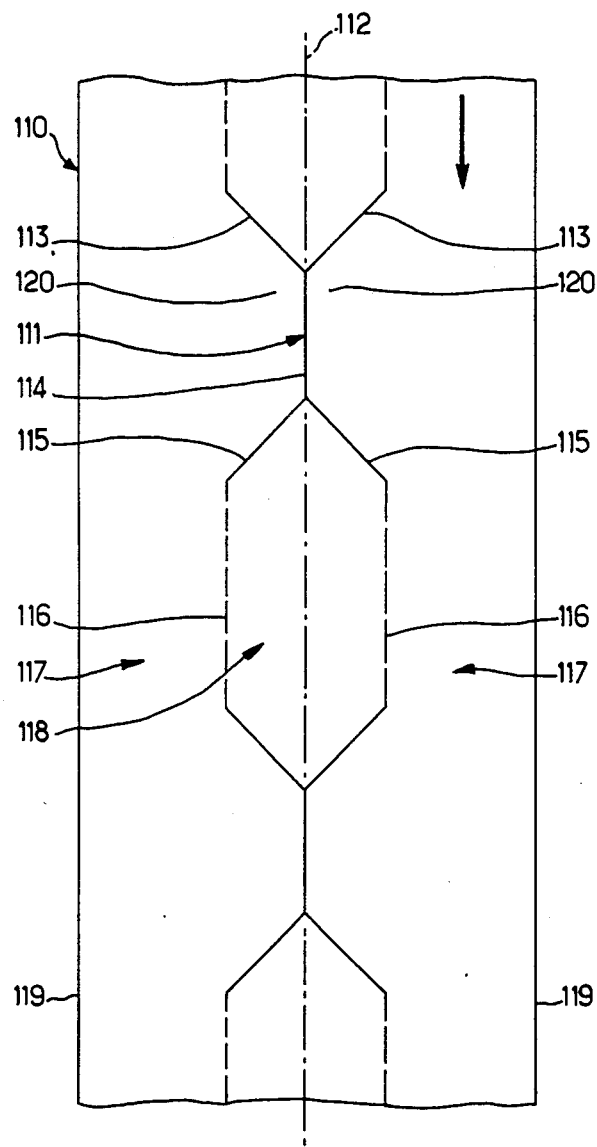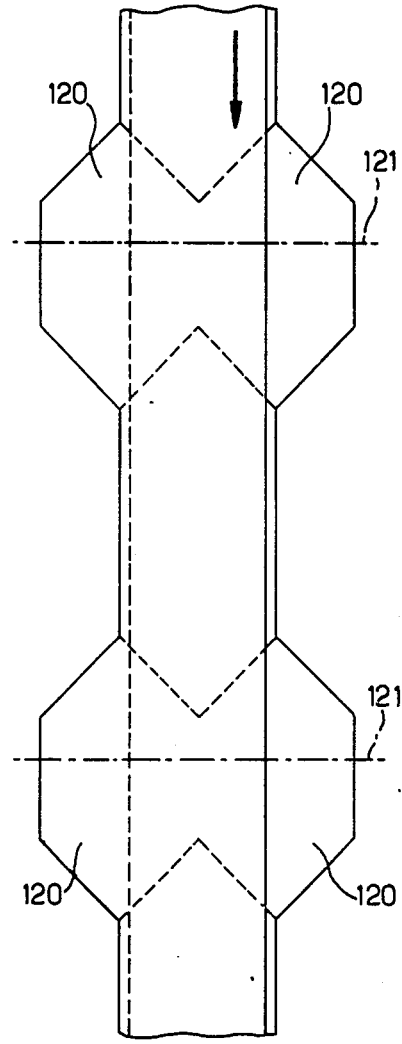

EGG TIMER-SHAPED ABSORBENT PAD FOR A PAIR OF NAPPY-PANTS, AND PROCESS FOR THE CONTINUOUS MANUFACTURE OF SUCH PADS

The present invention relates to an egg timer-shaped absorbent pad, i.e. having a rectangular general shape with two opposite lateral indentations, for a pair of nappy-pants, as well as to a process for the continuous manufacture of such pads.

The egg timer-shaped absorbent pads comprise, in the direction of the length of the pad, two end zones and a between-the-legs intermediate zone of width smaller than that of the end zones. For reasons of effectiveness, it is desirable that these pads have, in the direction of the width, at least in the between-the-legs zone, a central part of thickness greater than that of the lateral parts.

Two embodiments of absorbent pads of this type are known.

According to a first embodiment, a pad consists of a rectangular section of a strip of absorbent material, in each of the two opposite lateral edges of which two incisions are made, the area demarcated between these two incisions being folded back in the direction of the opposite lateral edge, so that the two opposite flaps form a double thickness in the between-the-legs zone of the pad. This folding back does cause problems to some extent with the high rates of production. Moreover, this folding back must be carried out with a high degree of precision so that the free edges of the opposite flaps are contiguous. In fact, if this is not the case, these edges may either be spaced apart from each other, or overlap, which modifies the functioning of the absorbent pad as well as the appearance of the nappy-pants.

According to another known embodiment, an absorbent pad is formed by the superimposition of a rectangular section of absorbent material, which has a width smaller than or equal to the between-the-legs width of the complete absorbent pad, on an egg timer-shaped strip of absorbing material. For the continuous manufacture of such pads, a strip of absorbent material is cut out along a rectilinear longitudinal cutting line into a relatively narrow first partial strip and a wider second partial strip, opposite and equal indentations are then cut on this wider partial strip and the narrower partial strip is placed on the wider partial strip before cutting the composite strip thus formed in the transverse direction within the areas contained between successive indentations. The main disadvantage of this process, which also enables absorbent pads with double thickness in the between-the-legs zone to be obtained, lies in the waste due to the cuts made in the wider partial strip in order to obtain the indentations.

For reasons of effectiveness, it turned out that it would be desirable to have an even greater thickness, namely a triple thickness, in the between-the-legs zone. In principle, this result could be obtained by the combination of the two embodiments above, namely by cutting a strip of absorbent material along a rectilinear longitudinal cutting line into a narrow first partial strip and into a wider second partial strip, according to the second embodiment, by the conversion of the wider strip into a strip containing flaps according to the first embodiment, and by the superimposition of the narrower strip on this strip with flaps, in order to obtain thereby a triple thickness in the between-the-legs zone. However, such a process would still retain the disadvantages of the first embodiment, namely, especially the low rate of production.

The subject of the present invention is an egg timer-shaped absorbent pad which can be manufactured in a simple way, at a fast rate, without any waste, this pad comprising, in the median part of its width, especially in the between-the-legs zone, a thickness which is three times that of the lateral parts of the end zones.

The invention also relates to a particularly simple and rapid process for the continuous manufacture of such absorbent pads.

The egg timer-shaped absorbent pad according to the invention, with two opposite lateral indentations, for a pair of nappy-pants, comprising in the direction of its length, two end zones and a between-the-legs intermediate zone of width smaller than that of the end zones, consists of a rectangular piece of flat absorbent material which has, in the two end zones, incisions starting from the transverse edges and subjected to a double folding around two longitudinal folding lines extending between the inner ends of the said incisions, so as to obtain a triple thickness of the absorbent material at least on the median part of the width of the between-the-legs zone and a single thickness of the absorbent material in the lateral parts of the end zones.

Depending on whether the between-the-legs zone should have a triple thickness of absorbent material over all or part of its length, the distance between the two longitudinal folding lines is equal to or greater than the distance separating each of these folding lines from the corresponding longitudinal edge of the rectangular piece of absorbent material.

According to a first embodiment, the incisions, in each end zone of the pad, consist of two incisions which are symmetrical at the longitudinal median line of the rectangular piece, converging from a transverse edge of this end zone in the direction of the opposite end zone.

According to a second embodiment, the incisions, in each end zone of the pad, consist of two incisions which are symmetrical at the longitudinal median line of the rectangular piece, diverging from the transverse edge of this end zone in the direction of the opposite end zone.

According to the first embodiment, the two incisions may advantageously each contain a longitudinal straight line segment starting from the transverse edge and followed by an inclined straight line segment.

According to the second embodiment, the two incisions may advantageously contain a common longitudinal straight line segment, starting from the transverse edge, extending along the longitudinal median line of the rectangular piece, and followed by two diverging straight line segments.

For the continuous manufacture of absorbent pads according to the first embodiment, the following operations are carried out in sequence: in a continuous strip of absorbent material, of width greater than the maximum width of the pads to be manufactured, at intervals corresponding to the length of the pads to be manufactured, two opposite incisions symmetrical in relation to the longitudinal median line of the strip and comprising, in the direction of the length of the strip, two diverging parts followed by two longitudinal parts followed by two converging parts are made, the two parts of the strip situated between each incision and the longitudinal lines connecting between them the successive incisions on the one hand, and the corresponding longitudinal edge of the strip on the other, are folded over each other around the said longitudinal lines and over the part of the strip situated between the said lines, and the folded strip is cut in the transverse direction at intervals corresponding to the length of the pads to be manufactured, at the place where the mutual distance between the two opposite incisions is maximal.

For the continuous manufacture of pads according to the second embodiment, the following operations are carried out in sequence: in a continuous strip of absorbent material, of width greater than the maximum width of the pads to be manufactured, at intervals corresponding to the width of the pads to be manufactured, two incisions symmetrical in relation to the longitudinal median line of the strip and comprising, in the direction of the length of the strip, two converging parts followed by a longitudinal median part followed by two diverging parts are made, the two parts of the strip situated between each incision and the longitudinal lines connecting between them the successive incisions on the one hand, and the corresponding longitudinal edge of the strip on the other, are folded over each other around the said longitudinal lines and over the part of the strip situated between the said lines, and the folded strip is cut in the transverse direction at intervals corresponding to the length of the pads to be manufactured, at the place where the mutual distance between the two opposite incisions is maximal.

In the first case, it is possible to fold the two lateral parts over each other on the median part. On the other hand, in the second case, it is advantageous to fold the strip into Z, i.e. first the median part with one of the lateral parts in one direction over the other lateral part and then to fold this other part in the opposite direction over the median part superimposed on the first lateral part.

Two embodiments of the subject of the invention will be described hereinafter, in greater detail, referring to the drawings attached; in the drawings:

FIGS. 7 and 8 represent, on a smaller scale, two stages of the process for the continuous manufacture of absorbent pads according to FIGS. 5 and 6.

Figure 1:
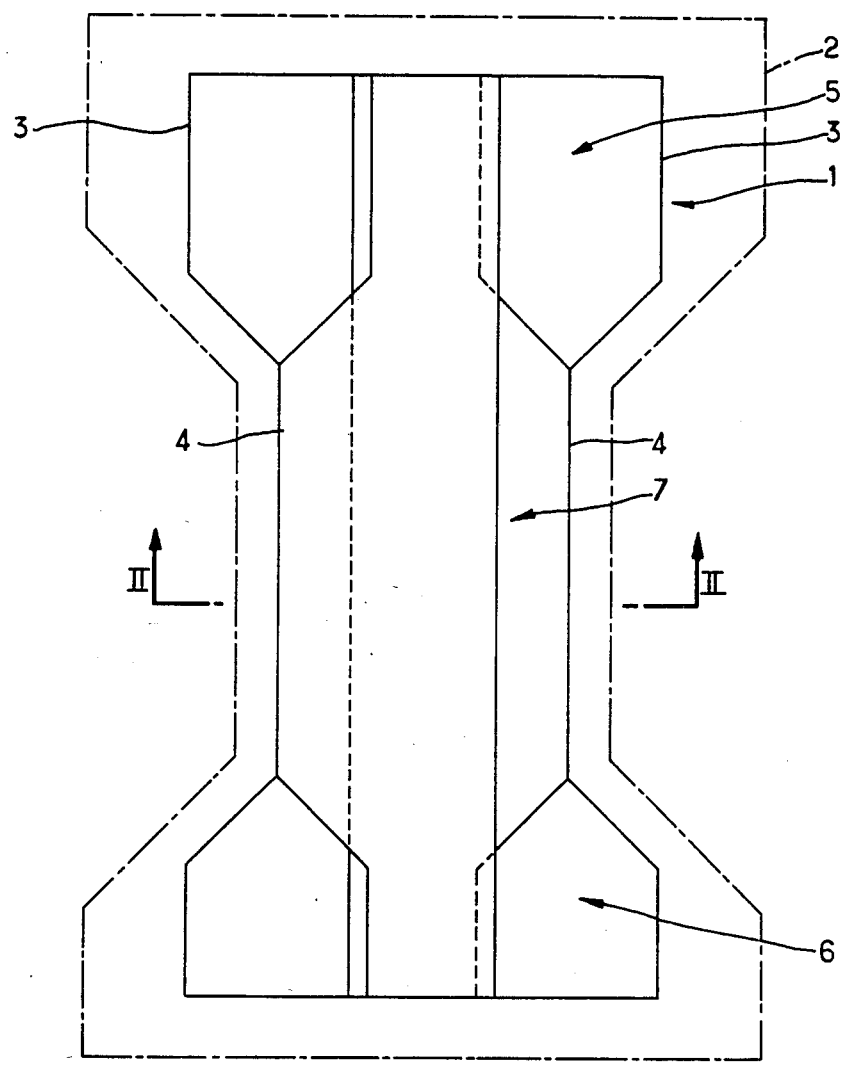
FIG. 1 is a top view of a first embodiment of an absorbent pad according to the invention.

According to FIG. 1, an absorbent pad 1 intended to be incorporated into a pair of nappy-pants 2 of which only the contour is indicated by dot-and-dash lines on FIG. 1 has, as does the pair of nappy-pants 2, the shape of an egg timer, known per se. This egg timer shape is due to the presence, in each of the two opposite longitudinal edges 3 of the pad 1, of a cut 4 in the shape of a trapezoidal indentation. The absorbent pad 1 thus comprises a rear end part 5, a front end part 6 and a between-the-legs intermediate part 7 situated between the two indentations 4. It is recognised from FIG. 1 that the rear end part 5 may, in a way known per se, be somewhat higher than the front end part 6. For fastening the nappy-pants, the rear end part 5 may, in a known way, be provided with adhesive fasteners, not shown.

Figure 2:
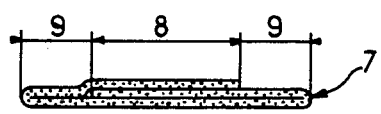
FIG. 2 is a section along II—II of FIG. 1.

According to FIGS. 1 and 2, the absorbent pad 1 formed from a rectangular piece of flat absorbent material has a triple thickness in the median part 8 of the width of the between-the-legs zone 7 and a double thickness in the two lateral parts 9 of the between-the-legs zone 7. In the two end zones 5 and 6, the pad also has a triple thickness in the median part and a single thickness in the lateral part.

Figure 3:
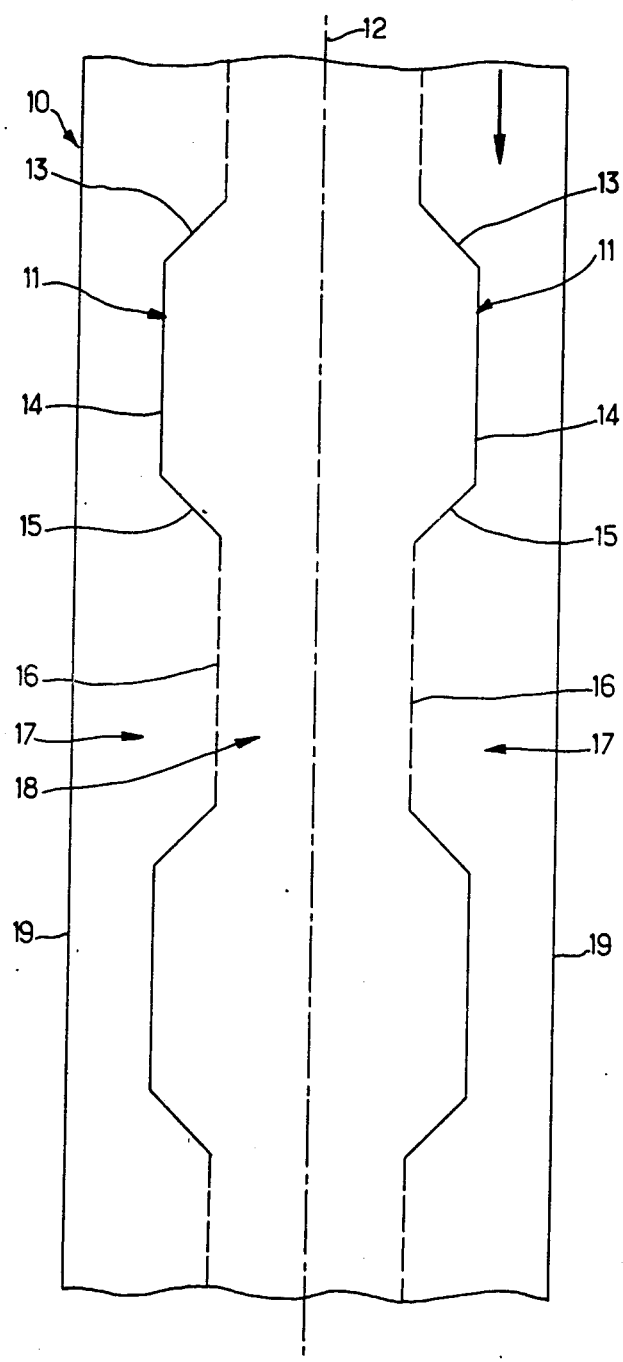
FIGS. 3 and 4 represent, on a smaller scale, two stages of the process for the continuous manufacture of absorbent pads according to FIGS. 1 and 2.

For the continuous manufacture of absorbent pads according to FIGS. 1 and 2, two opposite incisions 11, symmetrical in relation to the longitudinal median line 12 of the strip 10 are made, according to FIG. 3, in a strip 10 of absorbent material, in the course of unwinding the strip, successively, at intervals corresponding to the length of the pads to be manufactured. The two incisions 11 comprise, in the direction of unwinding the strip 10, two diverging straight line segments 13, followed by two longitudinal straight line segments 14 which are themselves followed by two converging straight line segments 15. In addition to these incisions 11, two longitudinal folding lines 16, extending between the ends of the successive incisions 11, are secured on the strip 10. It is noteworthy that the distance between the longitudinal straight line segments 14 of the opposite incisions 11 is equal to the maximum width of the absorbent pads 1 in the end zones 5 and 6, whereas the distance between the opposite folding lines 16 is equal to the width of the absorbent pad 1 in the between-the-legs zone 7 (see FIGS. 1 and 2). As a result, the distance separating each longitudinal folding line 16 from the corresponding longitudinal edge 19 of the strip 10 is less than the distance separating the two opposite folding lines 16.

Figure 4:
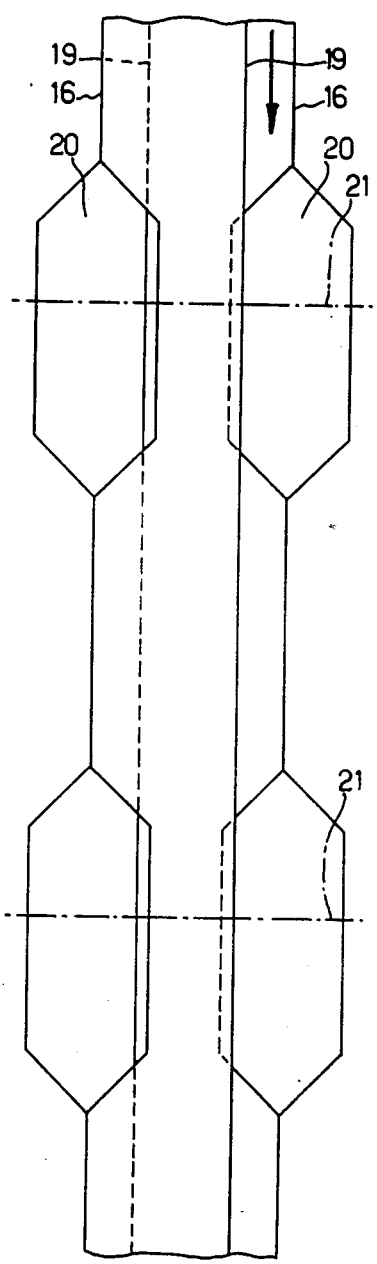

After securing the incisions 11 and the folding lines 16, the two lateral parts 17 demarcated in the strip 10 by the folding lines 16 and the incisions 11 on the one hand, and the corresponding longitudinal edges 19 of the strip 10 are continuously pressed down towards the inside, around the folding lines 16, successively one after the other, on the central part 18 demarcated between the folding lines 16 and the incisions 11 on the other hand, to form a strip as illustrated in FIG. 4, so that the two lateral parts 17 overlap on the central part 18. The strip thus folded comprises, at intervals, opposite lateral ears 20 of single thickness, due to the incisions 11.

It then suffices to cut the folded strip by cuts 21 in the transverse direction, opposite the ears 20, at intervals corresponding to the length of the absorbent pads to be manufactured. It is noticed on FIG. 4 that the transverse cutting lines 21 do not pass through the middle of the length of the ears 20, which enables absorbent pads having two end zones of different heights, as represented on FIG. 1, to be obtained.

Figure 5:
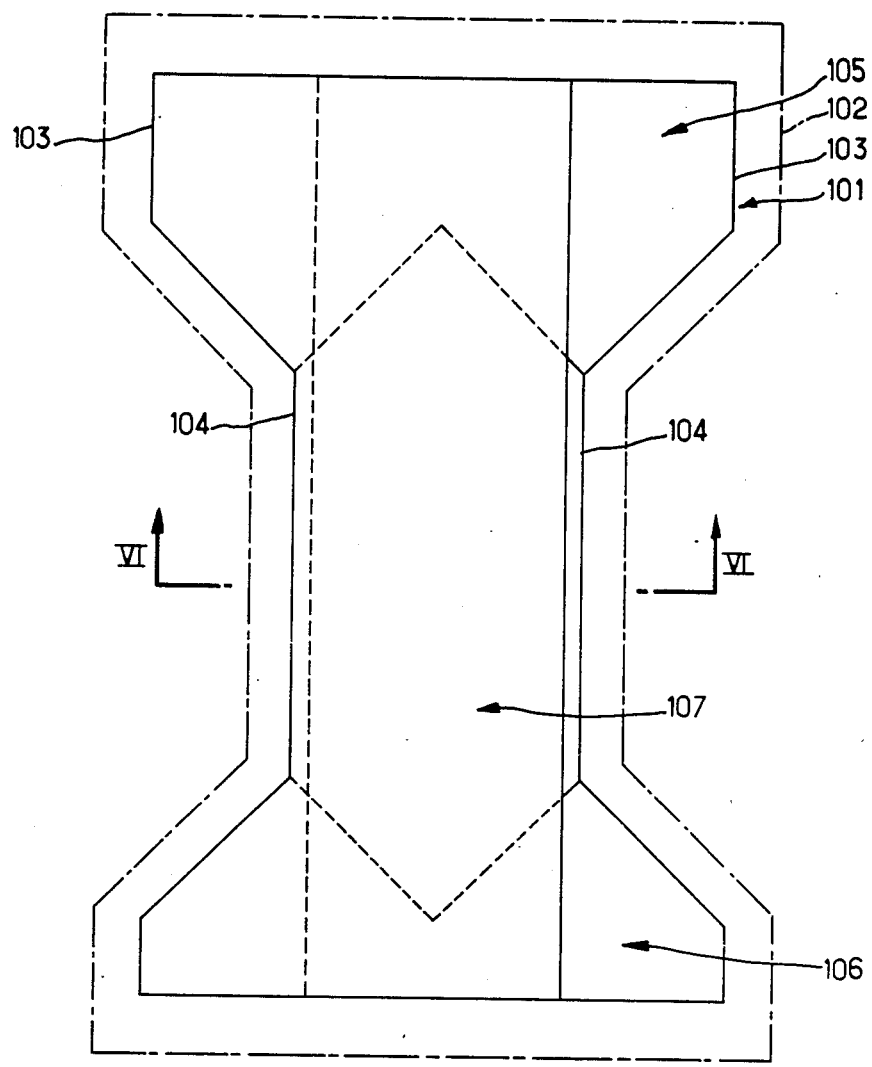
FIG. 5 is a top view of a second embodiment of an absorbent pad according to the invention.

The absorbent pad 101 according to FIG. 5 has the same general shape as the pad 1 of FIG. 1. This pad intended for a pair of nappy-pants 102 indicated schematically by its contour, is also egg timer-shaped and comprises, in each of its two opposite longitudinal edges 103, a cut 104 in the form of a trapezoidal indentation, which defines a rear end zone 105, a front end zone 106 and a between-the-legs intermediate zone 107 situated between the two indentations 104.

Figure 6:
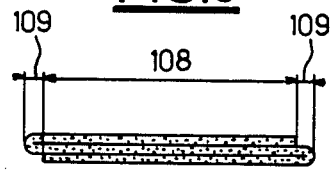
FIG. 6 is a section along VI—VI of FIG. 5.

Moreover, as shown on FIGS. 5 and 6, a median part 108 of triple thickness and two lateral parts 109 of double thickness are obtained in the direction of the width of the between-the-legs zone 107.

The pad 101 differs from the pad 1 of FIG. 1 mainly by the fact that the part 108 of triple thickness does not extend over the entire length of the pad 101, but is restricted substantially to the between-the-legs zone 107, whereas the end zones 105 and 106 are of double thickness in their median part and of single thickness in their lateral parts.

For the continuous manufacture of the absorbent pads according to FIGS. 5 and 6, a recess 111 symmetrical in relation to the longitudinal median axis 112 of the strip 110 is made in a strip 110 of absorbent material, of a width greater than the width of the pads to be manufactured, successively at intervals corresponding to the length of the pads to be manufactured. Each recess 111 comprises in the direction of unwinding the strip 110, two straight line segments 113 converging on the line 112, followed by a single longitudinal straight line segment 114, which itself is followed by two diverging straight line segments 115. Successive incisions 111 and longitudinal folding lines 116 are also made on the strip 110, between the free ends of the straight line segments 113 and 115. In this way, the strip 110 is subdivided, between two successive incisions 111, by folding lines 116 into two lateral parts 117 situated between a folding line 116 and the corresponding longitudinal edge 119 of the strip 110 respectively, and a median part 118 situated between the two folding lines 116.

The strip 110 then continuously undergoes a folding around lines 116, namely a first folding of the median part 118 and of a lateral part 117 at the same time, around the opposite folding line 116, over the other lateral part 117, then a second folding of the first lateral part 117 around the other folding line 116 over the median part 118 (folding into Z), as seen especially on FIG. 6. In the embodiment represented, this double folding consists first of a folding towards the left, over the left lateral part 117, of the median part 118 and of the right lateral part 117, then of a folding towards the right of the only lateral part 117 initially on the right.

The particular advantage of this method of folding consists in the fact that it can be carried out in a simple manner while the strip advances on a support, this folding not being hindered by the "ears" 120 which, because of the shape of the incisions 111, extend over the lateral parts 117 beyond the folding lines 120 and which, after the double folding, project in single thickness over the double- and triple-thickness median part of the strip (see FIG. 8).

It then suffices to cut the strip along a cutting line 121 in the transverse direction at intervals corresponding to the length of the absorbent pads to be manufactured, at the place where the ears 120 are situated, in order to obtain individual absorbent pads. As indicated on FIG. 8, the cutting at 121 is not carried out in the middle of the length of the ears 120, in order to obtain thereby, as illustrated on FIG. 5, an absorbent pad having end zones of different height.

It is self-evident that the embodiments described above and illustrated with the drawings attached have only been given by way of non-limiting examples and that many modifications and variations are possible within the scope of the invention.

Thus, the incisions 11 and 111, instead of being formed by straight line segments, could also comprise incurved segments, which would give curvilinear indentations to the absorbent pads 1, 101.

Moreover, the between-the-legs zones 7, 107 could be of triple thickness over their entire width.

The absorbent pad according to the invention may be manufactured using any absorbent material in the form of a strip, for example cellulose foam or wadding ("fluff") with or without superabsorbent material incorporated and with or without lining materials such as paper and the like.

We claim:
1. Process for the continuous manufacture of egg timer-shaped absorbent pads, having a rectangular general shape with two opposite lateral indentations, for a pair of nappy-pants, comprising, in the direction of its length, two end zones and a between-the-legs intermediate zone of width smaller than and thickness greater than those of the end zones, characterized in that in a strip of absorbent material (10) of width greater than the maximum width of the pads to be manufactured, at intervals corresponding to the length of the pads to be manufactured, two opposite incisions (11) symmetrical in relation to the longitudinal median line (12) of the strip and comprising, in the direction of the length of the strip, two diverging parts (13), followed by two converging parts (15) are successively made, in that the two lateral parts (17) of the strip (10), included between each incision (11) and the longitudinal lines (16) connecting between them the successive incisions on the one hand, and the corresponding longitudinal edge (19) of the strip (10) on the other, are folded over each other around the said longitudinal lines and over the median part (18) of the strip situated between the said lines (16), and in that the strip thus folded is cut in the transverse direction at intervals corresponding to the length of the absorbent pads to be manufactured, at the place where the distance separating the opposite incisions (11) is maximal.

2. Process for the continuous manufacture of egg timer-shaped absorbent pads, having a rectangular general shape with two opposite lateral indentations, for a pair of nappy-pants, comprising, in the direction of its length, two end zones and a between-the-legs intermediate zone of width smaller than and of thickness greater than those of the end zones, characterized in that in a strip of absorbent material (110) of width greater than the maximum width of the pads to be manufactured, at intervals corresponding to the length of the pads to be manufactured, two incisions (111) symmetrical in relation to the longitudinal median line (112) of the strip and comprising, in the direction of the length of the strip, two converging parts (113) followed by two diverging parts (115) are successively made, in that the two lateral parts (117) of the strip (110), included between the incisions (111) and the longitudinal lines (116) connecting between them the successive incisions on the one hand, and the corresponding longitudinal edge (119) of the strip (110) on the other, are folded over each other around the said longitudinal lines and over the median part (118) of the strip, and in that the strip thus folded is cut in the transverse direction at intervals corresponding to the length of the absorbent pads to be manufactured, at the place where the distance separating the opposite incisions is maximal.

3. Process according to claim 2, characterized in that the strip (110) is folded into Z around the longitudinal lines (116).

4. Process according to any one of claims 1 to 3, characterized in that the longitudinal folding lines (16, 116) in the strip (10,110) are secured before folding.

5. Absorbent pad obtained by the implementation of the process according to claim 1 to 3.

6. Absorbent pad obtained by the implementation of the process according to any one of claims 2 to 3.

7. Nappy-pants comprising an absorbent pad according to claim 5.

8. Nappy-pants comprising an absorbent pad according to claim 6.

* * * * *